US010395560B2

(12) United States Patent
Groenewald

(10) Patent No.: US 10,395,560 B2
(45) Date of Patent: Aug. 27, 2019

(54) IMAGING PHANTOM FOR RADIATION BASED EQUIPMENT

(71) Applicant: Stellenbosch University, Stellenbosch (ZA)

(72) Inventor: Annemari Groenewald, Somerset West (ZA)

(73) Assignee: Stellenbosch University, Stellenbosch, WC (ZA)

( * ) Notice: Subject to any disclaimer, the term of this patent is extended or adjusted under 35 U.S.C. 154(b) by 167 days.

(21) Appl. No.: 15/555,932

(22) PCT Filed: Mar. 2, 2016

(86) PCT No.: PCT/IB2016/051165
§ 371 (c)(1),
(2) Date: Sep. 5, 2017

(87) PCT Pub. No.: WO2016/142812
PCT Pub. Date: Sep. 15, 2016

(65) Prior Publication Data
US 2018/0047303 A1 Feb. 15, 2018

(30) Foreign Application Priority Data
Mar. 6, 2015 (ZA) .................. 2015/01528

(51) Int. Cl.
*G09B 23/28* (2006.01)
*A61B 6/00* (2006.01)
*A61B 6/03* (2006.01)

(52) U.S. Cl.
CPC ............ *G09B 23/286* (2013.01); *A61B 6/502* (2013.01); *A61B 6/583* (2013.01); *A61B 6/03* (2013.01); *G06T 2207/30168* (2013.01)

(58) Field of Classification Search
CPC .......... A61B 6/03; A61B 6/502; A61B 6/583; G06T 2207/30168; G09B 23/286
See application file for complete search history.

(56) References Cited

U.S. PATENT DOCUMENTS

| 5,095,499 A | 3/1992 | Wentz |
| 5,544,238 A | 8/1996 | Galkin |
| (Continued) | | |

FOREIGN PATENT DOCUMENTS

| CN | 202821387 U | 3/2013 |
| CN | 104076310 | 10/2014 |

OTHER PUBLICATIONS

CIRS: "CBCT Electron Density & Image Quality Phantom System Model 062M, 062MA, 062MQA", (Jan. 1, 2013).
(Continued)

*Primary Examiner* — Mark R Gaworecki
(74) *Attorney, Agent, or Firm* — Craig J. Lervick; Larkin Hoffman Daly & Lindgren, Ltd.

(57) ABSTRACT

A versatile phantom provides image quality control on multiple different types of medical x-ray imaging equipment. The phantom has a radiolucent housing including a first series of elements of the same shape and size wherein each element has a different electron density such that grey scale can be evaluated. A second series of elements of the same shape and material has a range of different sizes for assessing low contrast detectability. At least one position indicating item is selected from a central ball within the housing, position indicating lines on the housing and a unique flat peripheral face of the housing. The phantom also has at least one mammography dedicated item selected from elements representative of mammography fibers and mammography micro-calcifications. An instruction manual and optional result analysis program provides for semi-auto- (Continued)

matic result analysis for analyzing results and recommending corrective action for test results that are out of tolerance.

12 Claims, 2 Drawing Sheets

(56) References Cited

U.S. PATENT DOCUMENTS 5,719,916 A 2/1998 Nelson et al.
7,056,019 B1 6/2006 Hanson et al.

OTHER PUBLICATIONS

Q A Collectible: "Mammography Phantom Image Quality Evaluation", Sep. 1, 2008 (Sep. 1, 2008), pp. 1-7.
Jannetta A et al: "Mammographic image restoration using maximum entropy deconvolution", arxiv.org, Cornell University Library, 201 Olin Library Cornell University Ithaca, NY 14853, May 24, 2005 (May 24, 2005).
Written Opinion of the International Searching Authority of PCT/IB2016/051165, pp. 1-7, dated Sep. 12, 2017.

a b c

IMAGING PHANTOM FOR RADIATION BASED EQUIPMENT

CROSS-REFERENCE(S) TO RELATED APPLICATIONS

This application claims priority from South African provisional patent application number 2015/01528 filed on Mar. 6, 2015, which is incorporated by reference herein.

FIELD OF THE INVENTION

This invention relates to an imaging phantom for radiation based equipment and more particularly for the purpose of image quality analysis and quantification in equipment used for conducting general x-rays, fluoroscopy, mammography and computed tomography (CT) scanning.

Each of the activities identified may be used in the medical field to diagnose and monitor different disease conditions.

BACKGROUND TO THE INVENTION

Imaging phantom, or simply phantom, is a specially designed object that is scanned or imaged, especially in the field of medical imaging to evaluate, analyze, and tune the performance of various imaging devices. A phantom is more readily available and provides more consistent results than the use of a living subject or cadaver, and likewise avoids subjecting a living subject to direct radiation.

The image quality in carrying out imaging activities for diagnostic, monitoring or quality control purposes needs to be maintained at acceptable levels in order to prevent misdiagnosis and oversights in the medical field and malfunctioning of equipment in the industrial field. Image quality is defined and quantified in terms of contrast, resolution and noise in the image and these may be assessed quantitatively and qualitatively by routine imaging of suitable phantoms. Routine image quality assurance aids in identification of faulty equipment and hence promotes improved patient treatment or quality control in the industrial field.

As regards the medical field with which this invention is particularly concerned, each different type of equipment is typically provided with its own dedicated type of phantom so that the equipment can be calibrated and maintained so as to be most effective in use. However, such dedicated phantoms are typically proprietary to the manufacturer of the medical equipment concerned and generally have extremely limited application, typically only to that particular item of equipment used for a particular type of medical imaging. As a general rule, the cost of the phantoms is high consequent on limited numbers of production and the proprietary nature of the radiation based equipment concerned.

Different imaging modalities are used in diagnostic radiology in order to diagnose and follow up a variety of disease conditions. In order to ensure that the images obtained are of acceptable quality and can be used clinically for accurate diagnosis, image quality has to be evaluated and maintained. Image quality is a subjective concept that requires certain measures in order to be quantified, by using a phantom for example. Image quality is defined in terms of contrast, spatial resolution and noise by using various inserts, of different shapes, sizes and made from different materials, at fixed locations in the phantom, through visual inspection and by mathematical calculations.

Image contrast is the difference in the gray scales of adjoining regions in an image. It is affected by subject contrast, that is to say, the differences in signals before being registered as part of the image, detector contrast being how the detector converts the signal into output and digital image and display contrast in post-acquisition image processing.

Spatial resolution describes an imaging system's capability to distinguish two closely adjoining structures as separate as they become smaller and closer together, i.e. the amount of detail in the image. It is described by a point spread function (PSF), line-spread-function (LSF) or edge spread function (ESF) and these are used to calculate the modulation transfer function (MTF), which shows the percentage of an object's contrast as a function of its size.

Noise is a random "grainy" appearance in an image. Quantum noise is determined by the number of signals used to form the image and it influences the ability to detect low contrast objects.

The image quality parameters that have to be assessed with x-ray producing equipment in the diagnostic radiology environment therefore include grey scale linearity, circular symmetry, high contrast resolution, low contrast detectability, image uniformity, spatial resolution, image noise, scaling, magnification, distance measurements, contrast-detail relationships and the presence of artifacts, e.g. blurring. These parameters are assessed and quantified in CT scanning, mammography, fluoroscopy and x-ray imaging using a phantom with a variety of inserts. The obtained results are compared to baseline values. When image quality is not maintained, for example when images are blurred, contain artifacts, too much image noise and have poor low contrast detectability, small lesions and abnormalities can be missed.

X-ray photons can penetrate an object without undergoing an interaction, it can be completely absorbed in the object, thus contributing to dose and not to image formation, or it can be scattered. Photoelectric interactions only occur if the photon energy is greater than the binding energy of the electrons. All energy is transferred from photons to atomic shell electrons, which are ejected from the shell with certain energy. The ejected electrons spend their energy in the object, close to the original interaction site. The remaining vacancies are filled by higher shell electrons, producing characteristic x-rays. With Compton scatter a portion of the incident photon energy is absorbed and the photon is scattered through an angle. Contrast, due to differences in atomic numbers in a heterozygous object, depends strongly on the energy of the incident photon beam and thus on the beam kilo voltage (kV). At higher energies, where the photoelectric effect dominates, kV changes will have significant influences on contrast. In low atomic number materials, like the breast for example, lower kV settings are used for optimal contrast. With higher atomic number materials, like bone for example, the kV dependence of contrast is more pronounced over a wider kV range. In projection imaging a shadow image of the internal anatomy is projected on the image receptor, for example general x-rays, fluoroscopy and mammography. In CT scanning image reconstruction, from the photon penetration data, is used for image formation. The photons emerging through a heterozygous object contains an image of the object in terms of differences in attenuation through the different parts of the object. Here contrast is the amount of variation in the x-ray photons between different areas in the image. Hence the contrast is determined by the characteristics of the x-ray photon beam and the composition of the imaged object. Image receptors can either be x-ray film, CR plates or DR detectors.

Currently separate phantoms are used for image quality assurance in each of these imaging modalities. The ACR mammography phantom contains fibres (1.56, 1.12, 0.89, 0.75, 0.54, 0.40 mm in diameter), simulates tumorous masses with 2.00, 1.00, 0.75, 0.50, 0.25 mm diameter hemi-spheres and micro-calcifications with 0.54, 0.40, 0.32, 0.24, 0.16 mm speck groups. It is 4.2 cm thick and consists of 3.5 cm Lucite and a 0.7 cm thick paraffin insert, which contains the image quality indicators.

The NORMI 13 phantom has 7 dynamic steps, consisting of different thickness copper plates from 0.0 mm to 2.3 mm, for evaluation of contrast resolution. For low contrast evaluation, 6 disks with contrasts of 0.8% to 5.6% are visually inspected. It also evaluates grey scales, field size and image uniformity.

The NORMI Rad/Flu phantom incorporates a copper step wedge for grey scale assessment, a resolution test pattern, a grid plate and 8 low contrast detection inserts. Resolutions from 0.6 to 5.0 lppmm are included. Contrast is visually evaluated with a copper step wedge, with 17 steps of thickness 0.00 to 3.48 mm at depths of 13 mm and 5 mm. The phantom also evaluates position verification and distance measurements.

The Catphan phantom has two low contrast modules. The supraslice region has three groups of inserts, each with nine circular objects with diameters between 2 and 15 mm and contrast of 0.3, 0.5 and 1.0%. In the subslice module three groups of four inserts each are contained. Diameters range between 3 and 9 mm and contrast is fixed at 1.0%. The AAPM (American Association of Physicists in Medicine) report no 1 also suggests evaluating slice thickness with ramps placed in the phantom.

In resource limited hospitals and other medical facilities three main problems may be identified. The first of these is the cost of acquiring a number of different currently existing phantoms for each different type of proprietary equipment that needs to be tested or calibrated from time to time. The second problem is that of manpower and expertise as many hospitals and diagnostic radiology units do not have sufficiently well trained personnel such as medical physicists to do routine quality control with dedicated phantoms. In this regard, the results put out by current phantoms are not easy to analyze and interpret and this makes corrective action decisions difficult. Thirdly, there is the problem that conducting image quality result analysis and deciding on corrective action takes time and often needs to be done by qualified staff that are simply not available.

There is a need for an improvement to the present situation.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided a versatile phantom for image quality control on multiple different types of medical x-ray imaging equipment comprising a radiolucent housing in which there are located a first series of elements of the same shape and size wherein each element has a different electron density such that grey scale can be evaluated utilizing the series; a second series of elements of the same shape and material but having a range of different sizes for assessing low contrast detectability; at least one position indicating item selected from a central ball within the housing, position indicating lines on the housing and a unique flat peripheral face of the housing; and at least one mammography dedicated item selected from elements representative of mammography fibres and mammography micro-calcifications.

Further features of the invention provide for the radiolucent housing to have one or more of a circular disc having is faces parallel to major faces of the phantom, an inclined CT slice width ramp, and a resolution indicating ball for MTF calculation from PSF preferably accurately located relative to a central ball for distance measurement; for the position indicating items to include both of a central ball and position indicating lines on the housing of the phantom; for the phantom to be of squat right circular cylindrical shape in which instance the position indicating lines include two diametrically extending lines preferably crossing each other at right angles and preferably on each of two opposite circular faces thereof; and for the position indicating lines to include a peripheral line encircling sides of the phantom midway between two major faces thereof.

A phantom of the type defined above is intended to enable investigation to be carried out on all the required image quality parameters for the different x-ray imaging modalities with one exposure that is to be suitable for comprehensive image quality control. The inserts are located at fixed positions in the phantom and may be used for image quality quantification, without referring to user subjectivity, which is addressed by the data analysis program at least in instances in which tests like artefacts do not need to be assessed visually by a user.

The versatile phantom of this invention is targeted to undergo rigorous practical testing to ensure that it complies with and can measure the basic required image quality assessment parameters for the different applications, like signal-to-noise SNR, and contrast-to-noise CNR ratios and modulation transfer functions MTF.

The versatile phantom of this invention is able to be formulated to be used on multiple different types of x-ray producing equipment including general x-rays, fluoroscopy, mammography and CT scanners.

A stand may be provided for enabling the versatile phantom to be orientated in an upright orientation for CT scanning.

A user's manual will be provided to simplify use of the versatile phantom so that a clear and concise use of the phantom can be easily understood, with sufficient examples to assist in the process. The manual will describe how to set up the phantom up for quality control in each of multiple different modalities; how to establish baseline values for different items of equipment that are available; and how to perform the different quality control tests, including formulae for the quantitative evaluation of image quality.

A result analysis program is also provided for semi-automatic result analysis having a user friendly interface and which is programmed to automatically analyze results and recommend corrective action for test results that are out of tolerance. A user friendly interface is provided to allow for easy input of data. The result analysis program is configured to give a clear pass or fail output for the different tests and to give recommended corrective action and steps to be taken when results are out of tolerance.

The invention, a single phantom with associated user's manual and data analysis program, therefore provides a practical and versatile solution for basic performance evaluation, in terms of image quality quantification, of multiple major diagnostic radiology equipment in CT scanning, general x-ray imaging, fluoroscopy and mammography, that has the potential to save time and money and enable accurate quality control in remote hospitals with limited resources and limited suitably qualified staff.

In order that the invention may be more fully understood an extended discussion thereof follows with reference to the accompanying drawings.

DETAILED DESCRIPTION WITH REFERENCE TO THE DRAWINGS

Figure 1:
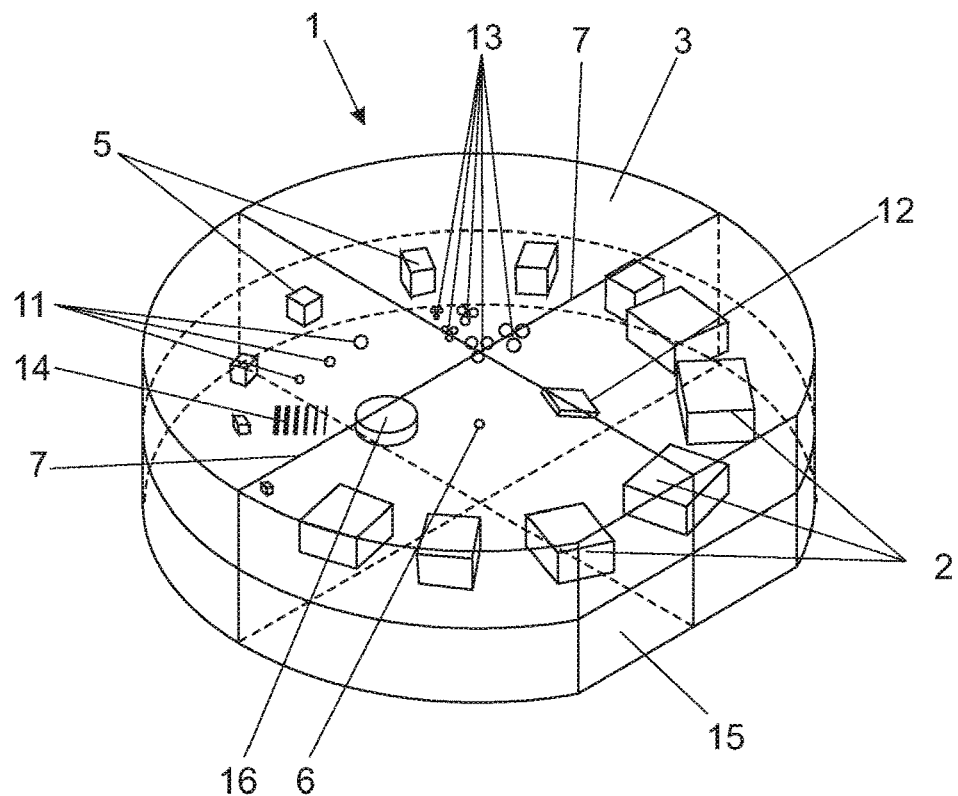
FIG. 1 is a schematic isometric view of one embodiment of versatile phantom according to the invention.
Figure 2:
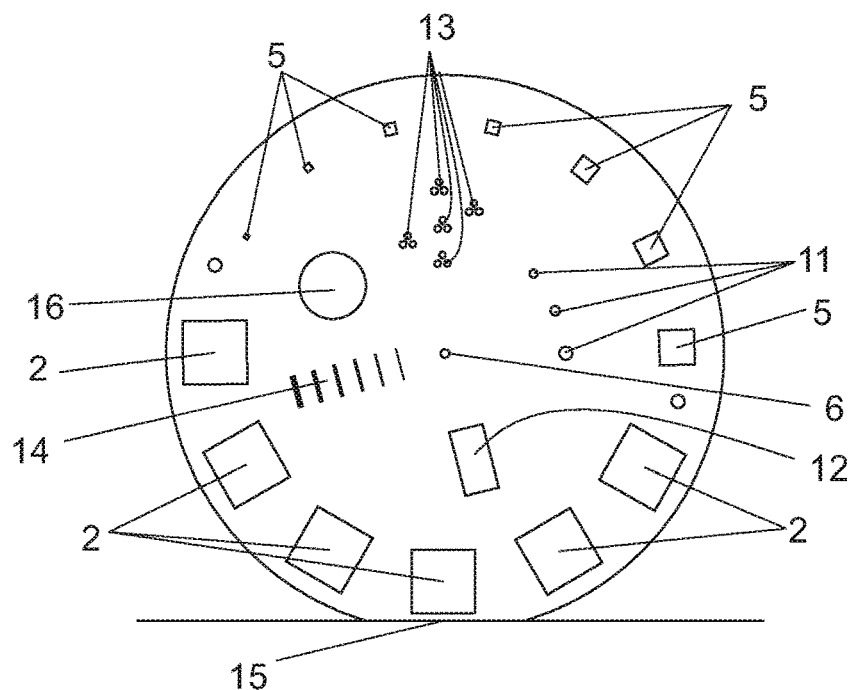
FIG. 2 is an elevation of a modified arrangement of a slight variation of the embodiment illustrated in FIG. 1 showing the phantom orientated on its flat side.
Figure 3:
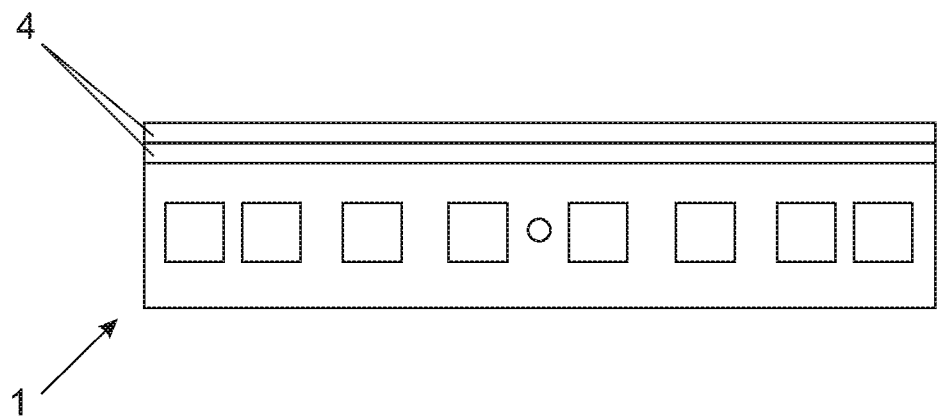
FIG. 3 is an edge view of the embodiment of the invention illustrated in FIG. 1 and illustrating additional plates for use in association therewith.

In general, the versatile phantom (1) of the invention may be circular in planar view with a flat side (15), as shown in FIGS. 1 and 2, with for example, a 170 mm diameter and 50 mm thickness. It may be constructed of a suitable high density polyethylene (HDPE), a suitable strength of polystyrene or a hard plastic, such as poly(methyl methacrylate) which is also known as PMMA or Perspex, as a housing material.

A first series of elements (2) of the same shape and size is embodied in the housing wherein each element of the first series has a different electron density for grey scale and Hounsfield Unit (HU) linearity evaluation and low contrast detectability. These elements may be blocks arranged with a face perfectly perpendicular to a phantom top surface (3) for planar imaging and a face perfectly perpendicular to the beam central axis for rotational imaging, i.e. computed tomography CT scanning. Seven to ten inserts of the same size, for example 15-20 mm, but made of different materials are proposed. In one instance six inserts are used with each measuring 20×20×10 mm. Proposed materials include PMMA (if not the housing material) polyethylene (if not the housing material), solid water, perspex (if not the housing material), polycarbonate, nylon, polystyrene (if not the housing material), teflon, plexiglass, lexan, Gammex SB3 bone tissue equivalent plastic, Gammex LN300 lung tissue equivalent plastic, Gammex solid water and air. One selection of materials for the first series of elements was PMMA, Teflon, Gammex SB3 bone, supawood, Gammex LN300 lung and air. These elements are arranged towards the phantom periphery.

It should be noted that spherical inserts would most likely be more ideal and easier to orientate due to circular symmetry in all directions but it is expected that the machining or other production of perfect spheres may be very expensive unless they can be effectively 3-D printed. Non-uniform attenuation of x-ray beam means large spheres will be needed for analysis. Blocks were thus proposed as a suitable alternative.

Two 20 mm thick or four 10 mm thick plates (4) made from the phantom housing material may be supplied in addition to the phantom itself so that they can be used with the phantom for automatic exposure control (AEC) evaluation and image uniformity assessment in planar imaging.

Computed tomography CT number or Hounsfield unit (HU) linearity may be investigated with the first series of elements of different densities and compositions that may be imaged with different grey scales, within the white to black spectrum. For example air is black, bone is white and different soft tissues exhibit a range of different grey colours on a computed tomography CT image. This test enables an assessment to be made of the differences that can be seen and if the colour assigned to each element (or tissue in human anatomy), remains constant with time. If grey scales change for a certain tissue type, this can lead to a misdiagnosis.

For set-up on a computed tomography CT couch a suitable stand will be supplied to position the phantom in the required upright position. This is necessary as diagnostic radiology computed tomography CT scanner couches do not generally have flat tops.

For CT scanning quality assurance the phantom may be set up on its flat side (15) as illustrated in FIG. 2. The following parameters may be assessed. Computed tomography low contrast detectability in order to investigate if objects with similar composition to the material of which it is made can be accurately identified, and to what degree. For example the smallest size of tumour embedded in normal tissue that can be diagnosed accurately and reproducibly may be assessed.

For this purpose, a second series of elements (5) that are all made from the same material, but are of different sizes, is employed. Possible materials provided that they are not used for the housing material include PMMA, polystyrene, perspex, nylon and teflon. Seven to ten of these elements will preferably be used. An example of thicknesses that are considered appropriate are 1, 2, 3, 4, 5, 6, 8, 10, 15 mm. These sizes correspond to recommendations in the literature and will be finalized based on machinability and cost. In one instance, eight inserts are being used of which one is the 20×20×10 mm one mentioned above as being used for the grey scales, and the seven additional ones are 10×10×10 mm, 8×8×8 mm, 6×6×6 mm, 4×4×4 mm, 3×3×3 mm 2×2×2 mm and 1×1×1 mm.

Computed tomography positioning accuracy, zero-slice and lasers may be assessed. In a reference coordinate system it is necessary to know that an object placed at a certain location will be reproducibly imaged at that correct location. This is referred to as the 0-slice or the position given to the CT scanner by an operator as the starting position. This position then has to transfer to the starting, or zero-slice position, in the computed tomography CT scan. The phantom has to be set up in the same manner each time for the data analysis program to work, as the program will search for certain objects at certain locations.

A small metallic bead (6), say 1 mm in diameter, is located exactly at the center of the phantom. Scribe lines (7) are provided on the phantom for set-up with lateral and top lasers. Once correctly set-up the scan zero may be set at this point. The metallic ball should appear at the centre or zero-slice.

Computed tomography image uniformity is also necessary to check. It is important that the grey scale, or colour of an object in an image, must be the same over the entire image when a uniform object, i.e. object made from the same material, is imaged. If the grey scale differs over the extent of the image it can lead to misdiagnosis. For example if a lung is imaged small changes in the grey scale from black (air) to dark grey (tissue) help identify lung tumours.

Four regions of interest (ROIs) of a specified size will be drawn at specified different locations in the central slice image. It is proposed that these regions of interest ROIs will be selected using a data analysis program as circles drawn on an image of the phantom using software. The mean and standard deviation in these are used to calculate image uniformity, i.e. the values in each of the regions of interest ROIs must be within a specified percentage of each other.

Artifacts in a computed tomography image are non-true objects in the image introduced by the imaging system and not present in the imaged object. They are highly undesirable. Such lines, blurs, streaks, dots, etc can lead to misdiagnosis. For example dust grains on the imaging plate can imitate micro-calcifications in a mammogram and lead to the false diagnosis of breast cancer. Blurring or ghost images can obstruct abnormal anatomy and diseases can be missed. The image may be visually inspected for the presence of artifacts, like streaks, dark or light bands, rings, ghost images, blurring due to motion and graininess due to quantum mottle.

Computed tomography signal to noise SNR and contrast-to-noise CNR ratios are to be monitored. Noise introduces graininess in an image, a mottled and unwanted effect. Contrast indicates on the difference in grey scale value between different objects, e.g. increasing the contrast makes it easier to distinguish between different objects. These ratios give a numerical value to the amount of noise and contrast in an image, related to the signal, or grey scale value, of a certain object. It indicates how clearly and easily different objects can be distinguished repeatedly. If the noise becomes too much and/or the contrast decreases, the image could be useless and could lead to misdiagnosis. These parameters have to remain constant for acceptable image quality.

Using an accompanying data analysis program, these ratios may be calculated with Equations 1 to 3, where $S_O$ and $\sigma_O$ are the mean signal and standard deviation of the noise of the object of interest and $S_B$ and $\sigma_B$ are that of the background area and A and B are the intensities in regions of interest ROIs of the same size inside and right next to the insert and CI is the standard deviation or noise in the regions of interest ROI next to the insert.

$$SNR = \frac{s_O}{\sigma_O} \quad \text{[Equation 1]}$$

$$CNR = \frac{s_O - s_B}{\sigma_B} \quad \text{[Equation 2]}$$

Computed tomography image resolution indicates the extent to which two objects can be distinguished as they become smaller and closer together. The higher the resolution of a system the smaller are the objects that it can resolve and accurately identify. The modulation transfer function is a complete descriptor of the resolution of an image, showing the ability of a system to identify separate objects graphically as a function of object size.

Metallic balls (11), 0.7, 0.5 and 0.35 mm in diameter, are used by the accompanying data analysis program to calculate the modulation transfer function MTF, from PSF. MTF completely describes the resolution of an image.

Computed tomography distance accuracy is important in that the obtained image has the same dimensions and scaling as the actual imaged anatomy. This test checks that scaling (as opposed to magnification) does not occur in the imaging process. This is important as distances are often measured from bony anatomy landmarks for surgical reference or sizes of lesions are measured for cancer staging. The distance between the resolution balls and the central ball will be accurately known and measured by the data analysis program to assess distance accuracy.

Computed tomography CT slice width options are available in a CT scanner. The smaller the slice width chosen, the more accurate is the computed tomography CT scan data, but the longer the scan takes and the greater the radiation dose that the patient receives. It is important to know that the chosen slice width is the actual slice width used in the scan. For example, if 5 mm is chosen and the actual scan is performed with 3 mm slices the patient will receive more radiation than should be the case.

A bone equivalent plastic ramp (12) is included having say a 20 mm length, a 10 mm wide and 3 mm thickness is placed in the phantom at an angle of 36-45°. The slice thickness may then be calculated with the data analysis program using the image of the ramps and known parameters. As an alternative, aluminium could be used for the ramp.

For planar imaging, i.e. mammography, general x-rays and fluoroscopy quality assurance, the phantom will be set up appropriately. The following parameters may be assessed for mammography.

The inserts as described in relation to computed tomography CT above may be used to visually determine the smallest visible element of the second series thereof, resembling a small mass in the breast with a grey scale similar to that of the surrounding breast tissue.

Small balls (13) or specs of metal, aluminum oxide, calcium carbonate, tungsten or silicon carbide can be used may simulate micro-calcifications. Suggested diameters range between 0.2 and 0.5 mm, for example 0.5, 0.4, 0.3 and 0.2 mm diameter. Groups of micro-calcifications indicate high risk tumour development areas. In one instance metallic wire cuttings or specks were chosen 0.5, 0.4, 0.3, 0.2, 0.1 mm in diameter, 3 in each group.

Mammography fibers (14) of nylon, or another suitable plastic, may be used in, for example, 10 mm length pieces of diameters ranging between 0.4 and 1.5 mm (for example 0.4, 0.6, 0.9, 1.2 and 1.5 mm) to simulate fibrous structures in the breast. This helps to identify ductal carcinoma, i.e. cancer that grows in the milk ducts. In one instance rubber bands were selected in 0.3, 0.4, 0.6, 0.9, 1.2 and 1.5 mm diameters Mammography low contrast detectability may be assessed as described in relation to computed tomography CT.

Mammography grey scale linearity assessment is as described in relation computed tomography CT.

Figure 4:
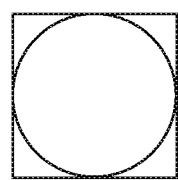
FIG. 4 is illustrates field sizes; a. in correct alignment; b. with the light field larger than the x-ray field; and c. with asymmetrical fields.
Figure 4:
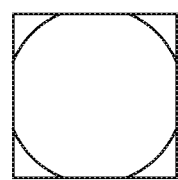
Figure 4:
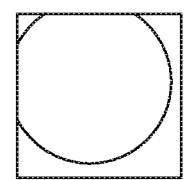

Mammography positioning accuracy, set-up and field size check may be carried out using the thin scribe lines (7) made centrally on the phantom on the planar imaging faces. Using these for set-up evaluates the displayed cross wire and system centering, that is to say, the central bead (6) should be at the center of the image. Setting a 170×170 mm field size implies that the entire phantom should appear in the image, as shown in FIG. 4. The image should be as shown in FIG. 4 with the central ball at the center of the image. FIG. 4b on the other hand shows the light field larger than the x-ray field and FIG. 4c illustrates a non-symmetrical field. It is important that the field size be correct as errors as in FIGS. 4b and c can lead to anatomy being excluded from the image and consequent misdiagnosis, or it may necessitate one or more retakes which result in increased radiation doses.

Mammography image uniformity may be evaluated using the data analysis program as described in relation to computed tomography. The additional 40 mm clear plates can be imaged. This image should be uniform, at the periphery and the center, as there are no attenuating inserts. Regions of interest ROI analysis on such an image with the data analysis program will be used to determine the degree of variation, i.e. non-uniformity, in the image.

The phantom image and the image of the additional 40 mm clear plated may be visually investigated for mammography image artifacts such as streaks, dark or light bands, ghosting, quantum mottle graininess or noise, blurring due to motion, lag or residual images from a previous exposure, and white specs indicating dead pixels in a digital system.

Mammography signal-to-noise SNR and contrast-to-noise CNR ratios are as described in relation to computed tomography.

As regards image resolution in mammography the resolution balls (11) as described in relation to computed tomography CT will show as a dot.

Modulation transfer function MTF may be calculated from point spread function PSF with the data analysis program from an image of the balls (11).

Mammography distance accuracy and circular geometry may be assessed as in relation to computed tomography. Circular geometry will be assessed with a 10 mm diameter and 3 mm thick plastic element (16), like poly(methyl methacrylate) PMMA, nylon or teflon. In one instance, PMMA was selected with a 20 mm diameter and 10 mm thickness. The data analysis program will determine the diameter of the imaged circle and compare it to the known diameter.

Mammography automatic exposure control AEC may be evaluated if the image quality, as described above is re-evaluated with 20 mm and then 40 mm of additional clear attenuator plates (4) placed on the phantom. Automatic exposure control AEC automatically determines the required imaging parameters, i.e. mAs and kV, to maintain image quality at a certain level as a patient or phantom thickness changes. The obtained image quality with 0, 20 and 40 mm additional attenuator on the phantom should be comparable if the automatic exposure control AEC works correctly. If automatic exposure control AEC does not work correctly it can result in poor quality images, leading to misdiagnosis or retakes and thus increased radiation doses. The phantom described above may be used to investigate the following factors for general x-rays and fluoroscopy.

X-ray low contrast detectability may be assessed as described in relation to computed tomography.

X-ray grey scale linearity may be assessed as described in relation to computed tomography.

X-ray positioning accuracy, set-up and field size check may be assessed as described in relation to mammography.

X-ray image uniformity may be evaluated as discussed in relation to mammography.

X-ray image artifacts may be treated as explained in relation to mammography.

X-ray signal to noise SNR and contrast-to-noise CNR ratios may be investigated as described in relation to computed tomography CT.

X-ray image resolution may be assessed as discussed in relation to mammography.

X-ray automatic exposure control AEC may be treated as described in relation to mammography.

X-ray circular geometry and distance accuracy may be assessed as discussed in relation to mammography.

In use the user will be required to set-up and image the phantom, as explained in detail with pictures and examples in a user's manual, to evaluate the obtained images visually as required and to load the images into the data analysis program to obtain the results semi-automatically. The user will also have to record these results, as explained in the manual. Based on the pass/fail outcome of the tests from the data analysis program, the user will have to perform more tests or call in a technician or medical physicist. It is, however, envisaged that the program will, at least in an advanced form, be programmed to recognize common deviations from a normal condition and will also be programmed to recommend to a user common ways in which the deviation can be corrected.

It will be understood that numerous variations may be made to what is described above without departing from the scope hereof. The number and variation of elements contained within the phantom can be varied according to requirements and each phantom may be made to the versatile within predetermined types of radiation based equipment.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A versatile phantom for image quality control on multiple different types of medical x-ray imaging equipment comprising a radiolucent housing in which there are located a first series of elements of the same shape and size wherein each element has a different electron density such that grey scale can be evaluated utilizing the series; a second series of elements of the same shape and material but having a range of different sizes for assessing low contrast detectability; at least one position indicating item selected from a central ball within the housing, position indicating lines on the housing and a unique flat peripheral face of the housing; and at least one mammography dedicated item selected from elements representative of mammography fibres and mammography micro-calcifications.

2. A versatile phantom as claimed in claim 1 in which the radiolucent housing has one or more of a circular disc having is faces parallel to major faces of the phantom, an inclined CT slice width ramp, and a resolution indicating ball for MTF calculation from PSF.

3. A versatile phantom as claimed in claim 2 in which resolution balls are accurately located relative to a central ball for distance measurement.

4. A versatile phantom as claimed in claim 1 in which the position indicating items include both a central ball and position indicating lines on the housing of the phantom.

5. A versatile phantom as claimed in claim 1 in which the phantom is of squat right circular cylindrical shape with an optional peripheral flat face in which instance any position indicating lines include two diametrically extending lines crossing each other.

6. A versatile phantom as claimed in claim 5 in which the position indicating lines cross each other at right angles and are present on each of two opposite circular faces of the phantom.

7. A versatile phantom as claimed in claim 1 in which position indicating lines include a peripheral line encircling sides of the phantom midway between two major faces thereof.

8. A versatile phantom as claimed in claim 1 in which the versatile phantom is able to assess basic required image quality parameters for different applications including one or more of signal-to-noise SNR, contrast-to-noise CNR ratios and modulation transfer functions MTF.

9. A versatile phantom as claimed in claim 1 in which the versatile phantom is formulated to be used on multiple different types of x-ray producing equipment including general x-rays, fluoroscopy, mammography and CT scanners.

10. A versatile phantom as claimed in claim 1 in which a stand is included for enabling the versatile phantom to be orientated in an upright orientation for CT scanning applications.

11. A versatile phantom as claimed in claim 1 in which a result analysis program is included for semi-automatic result analysis for analyzing results and recommending corrective action for test results that are out of tolerance.

12. A versatile phantom as claimed in claim 11 in which the result analysis program is configured to give a clear pass or fail output for different tests.

\* \* \* \* \*